US00PP23120P2

(12) United States Plant Patent

Klemm et al.

(10) Patent No.: US PP23,120 P2

(45) Date of Patent: Oct. 16, 2012

(54) *LOBELIA* PLANT NAMED 'KLELE10670'

(50) Latin Name: *Lobelia erinus*
Varietal Denomination: KLELE10670

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 33 days.

(21) Appl. No.: 13/065,798

(22) Filed: Mar. 30, 2011

(51) Int. Cl.
*A01H 5/00* (2006.01)

(52) U.S. Cl. ..... Plt./451

(58) Field of Classification Search ..... Plt./451
See application file for complete search history.

*Primary Examiner* — Susan McCormick Ewoldt

(74) *Attorney, Agent, or Firm* — Jondle & Associates, P.C.

(57) ABSTRACT

A new *Lobelia* plant named 'KLELE10670' particularly distinguished by its intensive pastel blue flower color and its good outdoor performance, is disclosed.

1 Drawing Sheet

Genus and species: *Lobelia erinus*.
Variety denomination: 'KLELE10670'.

BACKGROUND OF THE NEW PLANT

The present invention comprises a new and distinct variety of *Lobelia*, botanically known as *Lobelia erinus*, and hereinafter referred to by the variety name 'KLELE10670'. The new variety resulted from an open-pollination in June 2005 in Stuttgart, Germany between the proprietary female parent, *Lobelia* plant '05 0047' (unpatented), and an un-known male. A single plant selection was subsequently chosen for further evaluation and asexual propagation.

The new variety was first propagated via vegetative cuttings and in vitro propagation in May 2006 in Stuttgart, Germany, and has been asexually reproduced repeatedly by vegetative cuttings for more than fifteen generations. 'KLELE10670' has been found to retain its distinctive characteristics through successive asexual propagations via vegetative cuttings.

Plant Breeder's Rights for this variety were applied for in Canada on Mar. 19, 2010. 'KLELE10670' has not been made publicly available more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. Intensive pastel blue flower color; and
2. Good outdoor performance.

DESCRIPTION OF PHOTOGRAPH

This new *Lobelia* plant is illustrated by the accompanying photograph which shows overall plant habit including blooms, buds, and foliage of the plant in full color. The colors shown are as true as can be reasonably obtained by conventional photographic procedures. The photograph was taken in the Spring of 2010 of a 3-month-old *Lobelia* plant grown in a 10 centimeter pot in a glass greenhouse in Stuttgart, Germany under normal horticultural practices.

DESCRIPTION OF THE NEW VARIETY

The following detailed descriptions set forth the distinctive characteristics of 'KLELE10670'. The data which define these characteristics were collected from asexual reproductions carried out in Stuttgart, Germany. The plant history was taken in the Spring of 2010 of 3-month-old plants grown in 10 centimeter pots in a glass greenhouse with a minimum pinch date of eight weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Botanical.*—*Lobelia erinus.*
- *Common name.*—*Lobelia.*

Parentage:
- *Female parent.*—The proprietary *Lobelia* plant '05 0047' (unpatented).
- *Male parent.*—Unknown.

Growth:
- *Growth and branching habit.*—Half-hanging.
- *Form.*—Rounded.
- *Height* (*measured from the top of the soil including any flowers*).—11.0 cm.
- *Width* (*horizontal plant diameter, including any flowers*) .—20.0 cm.
- *Time to produce a finished flowering plant.*—10 weeks.
- *Outdoor plant performance.*—Good.
- *Time to initiate roots.*—3 weeks.
- *Root description.*—Fine, white roots, freely branching and dense.

Leaves:
- *Arrangement.*—Alternate.
- *Color.*—Immature Leaf: Upper surface: RHS 143B. Lower surface: RHS 143C. Mature Leaf: Upper surface: RHS 137B. Lower surface: RHS 137D.

*Length*.—4.0 cm to 5.0 cm.
*Width*.—1.5 cm to 1.8 cm.
*Shape*.—Elliptical.
*Margin*.—Serrate.
*Apex*.—Obtuse.
*Base*.—Acute.
*Texture* (*both upper and lower surfaces*).—Smooth.
*Venation*.—Pinnate.

Stems:
*Length*.—*Approximately* 18.0 cm.
*Diameter*.—0.15 cm.
*Internode length*.—2.0 cm to 4.0 cm.
*Texture*.—Smooth.
*Stem anthocyanin*.—Absent.
*Peduncle*.—Length: 2.0 cm to 3.0 cm. Diameter: 0.03 cm to 0.04 cm. Texture: Smooth.

Flower buds:
*Shape*.—Inverse drop.
*Diameter*.—0.4 cm to 0.6 cm.
*Length*.—1.0 cm to 1.3 cm.

Inflorescence:
*Blooming habit*.—Continuous.
*Lastingness of individual blooms on plant*.—Approximately 1 week.
*Fragrance*.—Absent.
*Inflorescence type*.—Raceme.
*Quantity of flowers and buds per flowering branch*.—10 to 16.

Flowers:
*Flower diameter* (*horizontal*).—Approximately 1.8 cm.
*Flower height* (*vertical*).—Approximately 1.5 cm.
*Mature flower*.—Upper lobe: Color: Upper surface: RHS 100C. Length: Approximately 0.9 cm. Width: Approximately 1.0 cm. Shape: Obovate. Apex: Obtuse. Margin: Entire. Texture (both upper and lower surfaces): Smooth. Lower lobes: Color: Upper surface: RHS 100B and RHS NN155D. Length: Approximately 0.7 cm. Width: Approximately 0.2 cm. Shape: Obovate. Apex: Obtuse. Margin: Entire. Texture (both upper and lower surfaces): Smooth.
*Corolla tube*.—Color inside: RHS white with dark blue spots RHS 100A. Color outside: RHS 100C. Tube length: Approximately 1.0 cm. Diameter: 0.3 cm.
*Calyx*.—Length: Approximately 1.0 cm. Diameter: Approximately 1.5 cm. Shape: Funnel, star-shaped (sepals are fused in lower half). Apex: Acute. Texture: Smooth. Color: RHS 137A.

Reproductive organs:
*Androecium*.—Number of anthers: 5.
*Gynoecium*.—Pistil length: Approximately 0.5 cm.

COMPARISON WITH PARENTAL AND COMMERCIAL VARIETIES

'KLELE10670' differs from the female parent, '05 0047', (unpatented) in that 'KLELE10670' is half-hanging, whereas '05 0047' is upright. Additionally, 'KLELE10670' has light blue flowers, whereas '05 0047' has blue flowers.

'KLELE10670' differs from the commercial variety 'Hot Waterblue' (U.S. Plant Pat. No. 16,225) in that 'KLELE10670' has lighter blue flowers and green foliage, whereas 'Hot Waterblue' has darker blue flowers, and greyish green foliage. Additionally, 'KLELE10670' is half-hanging, whereas 'Hot Waterblue' is mounding.

We claim:

1. A new and distinct *Lobelia* plant named 'KLELE10670' as shown and described herein.

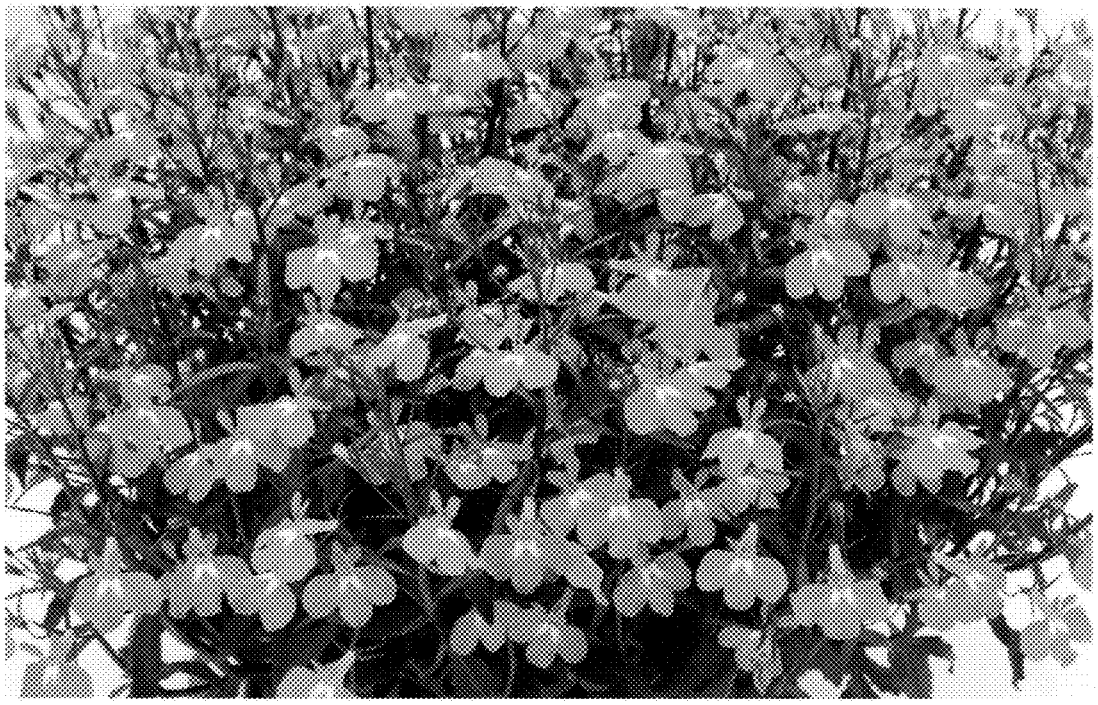

* * * * *